（12）United States Patent
Fusco et al.

US009315516B2

(10) Patent No.: US 9,315,516 B2
(45) Date of Patent: *Apr. 19, 2016

(54) BENZODITHIOPHENE DERIVATIVES AND THEIR USE AS PHOTOLUMINESCENT COMPOUNDS

(71) Applicant: Eni S.p.A., Rome (IT)

(72) Inventors: Roberto Fusco, Novara (IT); Paolo Biagini, San Giuliano Terme (IT); Stefano Maiorana, Milan (IT); Emanuela Licandro, Milan (IT)

(73) Assignee: ENI S.P.A. (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/364,131

(22) PCT Filed: Dec. 20, 2012

(86) PCT No.: PCT/IB2012/057516
§ 371 (c)(1),
(2) Date: Jun. 10, 2014

(87) PCT Pub. No.: WO2013/098726
PCT Pub. Date: Jul. 4, 2013

(65) Prior Publication Data
US 2014/0371463 A1 Dec. 18, 2014

(30) Foreign Application Priority Data
Dec. 28, 2011 (IT) .............................. MI2011A2405

(51) Int. Cl.
*C07D 495/04* (2006.01)
*H01L 31/055* (2014.01)
*C07D 519/00* (2006.01)
*C09K 11/06* (2006.01)
*H01L 31/0232* (2014.01)
*C09K 9/02* (2006.01)

(52) U.S. Cl.
CPC ............ *C07D 495/04* (2013.01); *C07D 519/00* (2013.01); *C09K 9/02* (2013.01); *C09K 11/06* (2013.01); *H01L 31/02322* (2013.01); *H01L 31/055* (2013.01); *C09K 2211/1037* (2013.01); *C09K 2211/1092* (2013.01); *C09K 2211/1096* (2013.01); *Y02E 10/52* (2013.01)

(58) Field of Classification Search
CPC ............................... C07D 495/04; H01L 31/055
See application file for complete search history.

(56) References Cited

U.S. PATENT DOCUMENTS

2011/0178255 A1    7/2011  Wigglesworth et al.

FOREIGN PATENT DOCUMENTS

WO       2011048458 A1    4/2011

OTHER PUBLICATIONS

Yuan et al. Journal of Polymer Science: Part A: Polymer Chemistry, 2011, 49, 701-711.*
Dutta et al. ACS Appl. Mater. Interfaces 2012, 4, 6669-6675.*
International Search Report dated Mar. 11, 2013 for PCT/IB2012/057516.
Christian B. Nielsen et al: A benzotrithiophene-based low band gap polymer for polymer solar cells with high open-circuit voltage 11, Journal of Materials Chemistry, vol. 21, No. 44, Jan. 1, 2011 p. 17642.
Robert C. Coffin et al: "Variation of the Side Chain Branch Position Leads to Vastly Improved Molecular Weight and OPV Performance in 4,8-dialkoxybenzo[1,2-b:4,5-b']dithiophene /2,1,3-benzothiadiazole Copolymers", Journal of Nanotechnology, vol. 2011, Jan. 1, 2011, pp. 1-10.
Ping Ding et al: "5,6-Bis(decyloxy)-2,1,3-benzooxadiazole-Based Polymers with Different Electron Donors for Bulk-Heterojunction Solar Cells". Journal of Physical Chemistry C, No. 32, Aug. 18, 2011, pp. 16211-16219.
Wanyi Nie et al: "A Soluble High Molecular Weight Copolymer of Benzo[1,2-b:4,5-b']dithiophene and Benzoxadiazole for Efficient Organic Photovoltaics", Macromolecular Rapid Communications, vol. 32. No. 15. Aug. 3, 2011, pp. 1163-1168.
Prakash Sista et al: "Synthesis, characterization, and computational modeling of benzodithiophene donor-acceptor semiconducting polymers", Journal of Polymer Science Part A: Polymer Chemistry, Jan. 1, 2011, figure 1; compounds P4, P6, table1.
Samuel C. Price et al: "Polycyclic Aromatics with Flanking Thiophenes: Tuning Energy Level and Band Gap of Conjugated Polymers for Bulk Heterojunction Photovoltaics", Macromolecules, vol. 43, No. 2, Jan. 26, 2010.
Bao Wang et al: "Naphthodithiophene-2,1,3-benzothiadiazole copolymers for bulk heterojunction solar cells", Chemical Communications, vol. 47, No. 33, Jan. 1, 2011, p. 9471.
Haifeng Wang et al: "Conjugated Polymers Based on a New Building Block: Dithienophthalimide", Macromolecules, vol. 44, No. 11, Jun. 14, 2011, pp. 4213-4221.
Mingjian Yuan et al: "Benzo[2,1-b;3,4-b??]dithiophene-based low-bandgap polymers for photovoltaic applications", Journal of Polymer Science. Part A, Polymer Chemistry, vol. 49, No. 3, Feb. 1, 2011, pp. 701-711.
Huaxing Zhou et al: "A weak donor-strong acceptor strategy to design ideal polymers for organic solar cells", ACS Applied Materials and Interfaces, American Chemical Society, US, vol. 2, No. 5, May 26, 2010, pp. 1377-1383.

(Continued)

*Primary Examiner* — Matthew Coughlin
(74) *Attorney, Agent, or Firm* — Abel Law Group, LLP

(57) ABSTRACT

Compound comprising a benzoetherodiazole group of formula (I) and at least one benzodithiophene group or a mixture of compounds comprising a benzoetherodiazole group and at least one benzodithiophene group of formulae (II) and (III). Both said compound and said mixture of compounds can be advantageously used as spectrum converters in luminescent solar concentrators (LSCs), capable, in their turn, of enhancing the performances of solar devices (i.e. devices for exploiting solar energy) such as, for example, photovoltaic cells, photoelectrolytic cells.

7 Claims, 1 Drawing Sheet

(56) References Cited

OTHER PUBLICATIONS

Xiao et al: "Conjugated polymers based on benzo[2,1-b:3,4-b]dithiophene with low-lying highest occupied molecular orbital energy levels for organic photovoltaics", PMSE Preprints, vol. 101, Jan. 1, 2009-Aug. 20, 2009, pp. 780-781.

Mikroyannidis J A et al: "Synthesis of benzoselenadiazole-based small molecule and phenylenevinylene copolymer and their application for efficient bulk heterojunction solar cells", Organic Electronics, Elsevier, Amsterdam, N L, vol. 11, No. 2, Feb. 1, 2010, pp. 311-321.

Velusamy M et al: "Organic dyes incorporating low-band-gap chromophores for dye-sensitized solar cells", Organic Letters, American Chemical Society, US, vol. 7, No. 10, Jan. 1, 2005, pp. 1899-1902.

Meijer E W et al: "Band-Gap Engineering of Donor-Acceptor-Substituted PI-conjugated polymers", Chemistry—A European Journal, Wiley-V C H Verlag GmbH & Co. KGAA, Weinheim, DE, vol. 4, No. 7, Jan. 1, 1998, pp. 1235-1243.

Turro et al.; "Modern Molecular Photochemistry of Organic Molecules" (2010), ISBN 978-1-891389-25-2, pp. 215-217.

Williams et al.; "Analyst" (1983), vol. 108, p. 1067.

Montali et al.; "Handbook of Photochemistry" (2006), Taylor & Francis Group, pp. 572-576.

Rigamonti, C. et al.; "Heterocycles" (2008), vol. 76, pp. 1439-1470.

Sundby C. et al.; "Arkivoc" (2001), vol. (x), pp. 76-84.

Ted M. Pappenfus et al: "PBC-DFT Applied to Donor-Acceptor Copolymers in Organic Solar Cells: Comparisons between Theoretical Methods and Experimental Data". Macromolecules. vol. 44. No. 7. Apr. 12, 2011, pp. 2354-2357.

Italian Search Report dated Jun. 25, 2012 for Application No. IT MI 2011 2405.

* cited by examiner

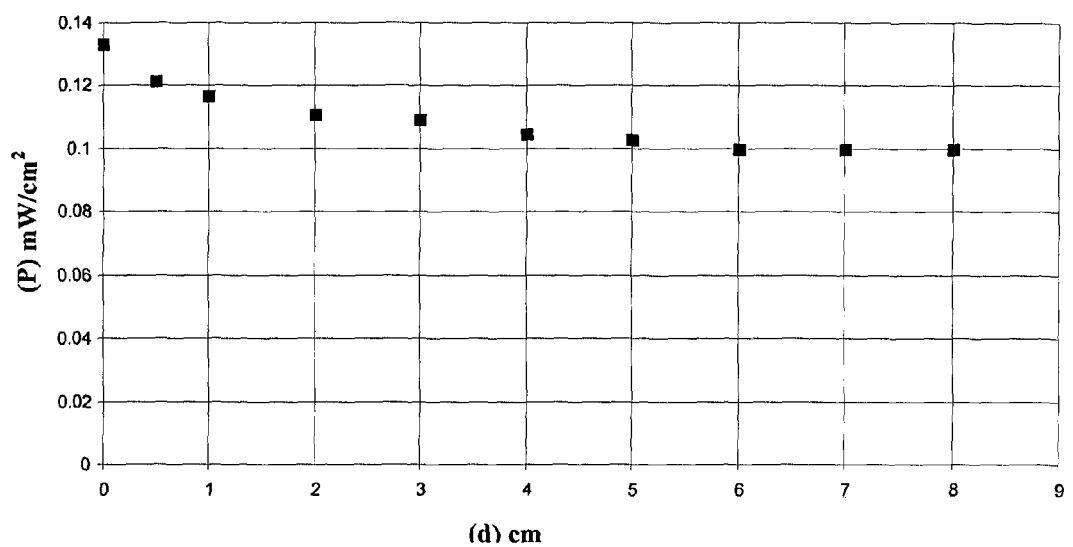

US 9,315,516 B2

BENZODITHIOPHENE DERIVATIVES AND THEIR USE AS PHOTOLUMINESCENT COMPOUNDS

The present invention relates to a photoluminescent compound or to a mixture of photoluminescent compounds.

More specifically, the present invention relates to a compound comprising a benzoetherodiazole group and at least one benzodithiophene group, or to a mixture of compounds comprising a benzoetherodiazole group and at least one benzodithiophene group.

Both said compound and said mixture of compounds, can be advantageously used as spectrum converters in luminescent solar concentrators (LSCs) capable, in their turn, of enhancing the performances of solar devices (i.e. devices for exploiting solar energy) such as, for example, photovoltaic cells, photoelectrolytic cells.

The present invention also relates to a luminescent solar concentrator (LSC) including at least one compound comprising a benzoetherodiazole group and at least one benzodithiophene group, or at least a mixture of compounds comprising a benzoetherodiazole group and at least one benzodithiophene group, and also to a solar device comprising said luminescent solar concentrator (LSC).

In the state of the art, one of the main limits in exploiting the energy of solar radiations is represented by the capacity of solar devices of optimally absorbing exclusively radiations having wavelengths within a narrow spectrum range.

Against a spectrum range of solar radiation extending from wavelengths of about 300 nm to wavelengths of about 2,500 nm, solar cells based on crystalline silicon, for example, have an optimum absorption area (effective spectrum) within the range of 900 nm-1100 nm, whereas polymer solar cells can be damaged when exposed to radiations with wavelengths lower than about 500 nm, due to induced photodegradation phenomena which become significant below this limit. The efficiency of the solar devices of the state of the art is typically at its maximum within the spectrum region ranging from 570 nm to 680 nm (yellow-orange).

The drawbacks previously mentioned imply a limited external quantum efficiency (EQE) of the solar device, defined as the ratio between the number of electron-hole pairs generated in the semiconductor material of the solar device and the number of photons striking the device.

In order to improve the external quantum efficiency (EQE) of solar devices, devices have been developed, i.e. luminescent solar concentrators (LSCs) which, when interposed between the light radiation source (the sun) and the solar device, selectively absorb striking radiations having wavelengths outside the effective spectrum of the device, re-emitting the energy absorbed in the form of photons having a wavelength within the effective spectrum. When the energy of the photons re-emitted by a luminescent solar concentrator (LSC) is higher than that of the striking photons, the photoluminescent process, comprising absorption of the solar radiation and subsequent re-emission of photons having a lower wavelength, is also called "up-conversion" process. When, on the contrary, the energy of the photons emitted by a luminescent solar concentrator (LSC) is lower than that of the striking photons, the photoluminescent process is called "down-shifting" process.

The luminescent solar concentrators (LSCs) known in the state of the art typically consist of a support made of material transparent, as such, to the radiations of interest (for example, polymeric or inorganic glasses), comprising photoluminescent compounds consisting of organic molecules or of metal complexes. In particular, the support is transparent to radiations having a frequency within the effective spectrum of the solar device.

Said spectrum converters can be deposited on the glass support as a thin film or, as in the case of polymeric materials, they can be dispersed inside the polymeric matrix. Alternatively, the polymeric matrix can be directly functionalized with photoluminescent chromophore groups.

Ideally, in order to be used in luminescent solar concentrators (LSCs), the spectrum converters must have the following characteristics:

high luminescence quantum efficiency ($\Phi$) [($\Phi$) is defined according to the following equation (1) as the ratio between the number of photons emitted and the number of photons absorbed by a luminescent molecule, per unit of time, and has a maximum value equal to 1]:

$$(\Phi) = \text{number of photons emitted/number of photons absorbed} \qquad (1);$$

wide absorption band in the spectral region where the solar device has a low efficiency;

high molar extinction coefficient ($\epsilon$);

narrow emission band in the spectral region where the solar device is mainly efficient;

absorption and emission bands well separated, i.e. a high Stokes shift defined as the difference, normally measured in frequency units ($cm^{-1}$), between the spectral positions of the maximum values of the absorption band and of the emission band, to prevent or minimize self-absorption phenomena.

It is known that some benzothiadiazole compounds, in particular 4,7-di-(thien-2'-yl)-2,1,3-benzothiadiazole (DTB), are fluorescent compounds which can be used as spectrum converters in luminescent solar concentrators (LSCs). Compounds of this type are described in international patent application WO 2011/048458.

4,7-di-(thien-2'-yl)-2,1,3-benzothiadiazole (DTB) is characterized by an emission centred around 579 nm, a value which corresponds to an energy well above the minimum functioning threshold of photovoltaic cells, a threshold which, for example, corresponds to a wavelength of about 1100 nm for the most widely-used cells, based on silicon. Furthermore, its absorption of light radiation is intense and extends over a relatively wide wavelength range, indicatively ranging from 550 nm (the wavelength of green radiation) to ultraviolet. Finally, 4,7-di-(thien-2'-yl)-2,1,3-benzothiadiazole (DTB) has a Stokes shift, in a solution of dichloromethane, equal to 133 nm (4250 $cm^{-1}$), much higher than those of most commercial products so far proposed for use in luminescent solar concentrators.

For these reasons, the use of 4,7-di-(thien-2'-yl)-2,1,3-benzothiadiazole (DTB) has made it possible to produce extremely high-quality luminescent solar concentrators (LSCs).

Although absorbing a significant part of the solar spectrum, 4,7-di-(thien-2'-yl)-2,1,3-benzothiadiazole (DTB), however, has a modest absorption in its greater wavelength regions, corresponding to yellow and red radiations which can therefore not be converted into others that can be more effectively utilized by photovoltaic cells. For this reason, it would be desirable to avail of compounds, that can be used as spectrum converters, having a high luminescence quantum efficiency ($\Phi$), an absorption spectrum extending more towards red, a high molar extinction coefficient ($\epsilon$) and a high Stokes shift.

The Applicant has therefore considered the problem of finding compounds that can be used as spectrum converters in luminescent solar concentrators (LSCs), capable of having as many as possible of the characteristics indicated above so as to be able to increase the number of photons that can be effectively converted into radiations which can be used by a solar device.

The Applicant has now found a compound comprising a benzoetherodiazole group and at least one benzodithiophene group, and also a mixture of compounds comprising a benzoetherodiazole group and at least one benzodithiophene group, that can be advantageously used as spectrum converters in luminescent solar concentrators (LSCs), capable, in their turn, of enhancing the performances of solar devices such as, for example, photovoltaic cells, photoelectrolytic cells.

Both said compound and said mixture of compounds have, in solution, high luminescence quantum efficiency values (Φ) (i.e. values>75%). Furthermore, both said compound and said mixture of compounds have high Stokes shift values [i.e. values>4200 $cm^{-1}$ in solution, or values>3000 $cm^{-1}$ in polymethylmethacrylate (PMMA) film]. Both said compound and said mixture of compounds also have high values of the highest energy band maximum in the emission spectrum [i.e. values>610 nm in solution, or values>580 nm in polymethylmethacrylate (PMMA) film]. Furthermore, both said compound and said mixture of compounds have high molar extinction coefficient values (i.e. values>18000 $M^{-1}cm^{-1}$). Both said compound and said mixture of compounds are therefore capable of increasing the number of photons that can be effectively converted into radiations that can be used by a solar device.

An object of the present invention therefore relates to a compound having general formula (I) or to a mixture of compounds having general formula (I):

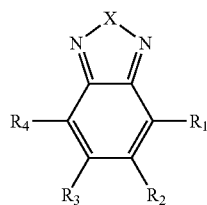

(I)

wherein:
X represents a heteroatom selected from oxygen (O), sulfur (S), selenium (Se), tellurium (Te), preferably sulfur (S);
$R_1$, $R_2$, $R_3$ and $R_4$, the same or different from each other, represent a hydrogen atom; or they represent a halogen atom such as, for example, fluorine, chlorine, bromine, preferably fluorine; or they are selected from linear or branched $C_1$-$C_{20}$, preferably $C_2$-$C_{12}$, alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, cyano groups; or they are selected from benzodithiophene groups having general formula (II) or (III):

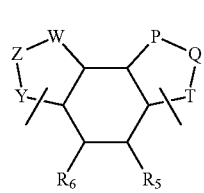

(II)

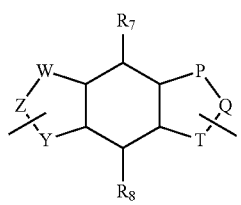

(III)

wherein:
Y, Z, W, P, Q and T, each independently, represent a sulfur atom (S), with the proviso that:
at least one of P, Q and T and at least one of W, Z and Y, is a sulfur atom (S); and
in general formula (III), Q and Z do not contemporaneously represent a sulfur atom (S);
the remaining among Y, Z, W, P, Q and T, represent a group —C—$R_9$, —C—$R_n$, —C—$R_{11}$, —C—$R_{12}$, so that the sum of the double carbon-carbon (C=C) bonds present in the two thiophene rings and in the benzene ring is equal to 5;
$R_5$, $R_6$, $R_7$, $R_8$, $R_9$, $R_{10}$, $R_{11}$ and $R_{12}$, the same or different from each other, represent a hydrogen atom; or they represent a halogen atom such as, for example, fluorine, chlorine or bromine, preferably fluorine or bromine; or they are selected from linear or branched $C_1$-$C_{20}$, preferably $C_2$-$C_{12}$, alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, cyano groups;
or $R_5$ and $R_6$, can be optionally bound to each other so as to form, together with the other atoms to which they are bound, a cycle containing from 3 to 12 carbon atoms, saturated, unsaturated, or aromatic, optionally substituted with linear or branched $C_1$-$C_{20}$ alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, cyano groups, said cycle optionally containing heteroatoms such as oxygen, sulfur, nitrogen, silicon, phosphorous, selenium;
or $R_1$ and $R_2$, $R_2$ and $R_3$, $R_3$ and $R_4$, preferably $R_2$ and $R_3$, can be optionally bound to each other so as to form, together with the other atoms to which they are bound, a cycle containing from 3 to 12 carbon atoms, saturated, unsaturated or aromatic, optionally substituted with linear or branched $C_1$-$C_{20}$ alkyl groups, optionally containing heteroatoms, aryl groups optionally substituted, heteroaryl groups optionally substituted, cycloalkyl groups optionally substituted, heterocyclic groups optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, cyano groups, said cycle optionally containing heteroatoms such as oxygen, sulfur, nitrogen, silicon, phosphorous, selenium;

with the proviso that at least one of $R_1$, $R_2$, $R_3$ and $R_4$, preferably at least two, even more preferably $R_1$ and $R_4$, represent(s) a benzodithiophene group having general formula (II) or (III).

For the purposes of the present description and of the following claims, the definitions of the numerical ranges always include the extremes, unless otherwise specified.

For the purposes of the present description and of the following claims, it should be noted that in general formula (II) and in general formula (III), for the sake of simplicity, the double carbon-carbon bonds (C═C) which, as specified above, must be such that their sum in the two thiophene rings and in the benzene ring is equal to 5, are not represented.

The term "$C_1$-$C_{20}$ alkyl groups" means linear or branched alkyl groups having from 1 to 20 carbon atoms, saturated or unsaturated. Specific examples of $C_1$-$C_{20}$ alkyl groups are: methyl, ethyl, n-propyl, iso-propyl, n-butyl, iso-butyl, t-butyl, pentyl, hexyl, heptyl, octyl, 2-ethylheptyl, 2-ethylhexyl, 2-butenyl, 2-pentenyl, 2-ethyl-3-hexenyl, 3-octenyl, 1-methyl-4-hexenyl, 2-butyl-3-hexenyl.

The term "$C_1$-$C_{20}$ alkyl groups optionally containing heteroatoms" means linear or branched alkyl groups having from 1 to 20 carbon atoms, wherein at least one of the hydrogen atoms is substituted by a heteroatom selected from: halogens such as, for example, fluorine, chlorine, bromine, preferably fluorine; nitrogen; sulfur; oxygen. Specific examples of $C_1$-$C_{20}$ alkyl groups optionally containing heteroatoms are: fluoromethyl, difluoromethyl, trifluoromethyl, trichloromethyl, 2,2,2-trifluoroethyl, 2,2,2-trichloroethyl, 2,2,3,3-tetrafluoropropyl, 2,2,3,3,3-pentafluoropropyl, perfluoropentyl, perfluorooctyl, perfluorodecyl, oxymethyl, thiomethyl, thioethyl.

The term "aryl groups" means aromatic carbocyclic groups. Said aromatic carbocyclic groups can be optionally substituted with one or more groups, the same or different from each other, selected from: halogen atoms such as, for example, fluorine, chlorine, bromine, preferably fluorine; hydroxyl groups; $C_1$-$C_{12}$ alkyl groups; $C_1$-$C_{12}$ alkoxyl groups; cyano groups; amino groups; nitro groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, bromophenyl, nitrophenyl, dimethylaminophenyl, naphthyl, phenylnaphthyl, phenanthrene, anthracene.

The term "heteroaryl groups" means aromatic heterocyclic groups, penta- or hexa-atomic, also benzocondensed or heterobicyclic, containing from 1 to 4 heteroatoms selected from nitrogen, oxygen, sulfur, silicon, selenium, phosphorus. Said heteroaryl groups can be optionally substituted with one or more groups, the same or different from each other, selected from: halogen atoms such as, for example, fluorine, bromine, chlorine, preferably fluorine; hydroxyl groups; $C_1$-$C_{12}$ alkyl groups; $C_1$-$C_{12}$ alkoxyl groups; cyano groups; amino groups; nitro groups. Specific examples of heteroaryl groups are: pyridine, methylpyridine, methoxypyridine, phenylpyridine, fluoropyridine, pyrimidine, pyridazine, pyrazine, triazine, tetrazine, quinoline, quinoxaline, quinazoline, furan, thiophene, hexylthiophene, bromothiophene, dibromothiophene, pyrrole, oxazole, thiazole, isooxazole, isothiazole, oxadiazole, thiadiazole, pyrazole, imidazole, triazole, tetrazole, indole, benzofuran, benzothiophene, benzooxazole, benzothiazole, benzooxadiazole, benzothiadiazole, benzopyrazole, benzimidazole, benzotriazole, triazolepyridine, triazolepyrimidine, coumarin.

The term "cycloalkyl groups" means cycloalkyl groups having from 3 to 30 carbon atoms. Said cycloalkyl groups can be optionally substituted with one or more groups, the same or different from each other, selected from: halogen atoms; hydroxyl groups; $C_1$-$C_{12}$ alkyl groups; $C_1$-$C_{12}$ alkoxyl groups; cyano groups; amino groups; nitro groups. Specific examples of cycloalkyl groups are: cyclopropyl, 2,2-difluorocyclopropyl, ciclobutyl, ciclopentyl, ciclohexyl, methylcyclohexyl, methoxycyclohexyl, fluorocyclohexyl, phenylcyclohexyl, decalin, abiethyl.

The term "heterocyclic groups" means rings having from 3 to 12 atoms, saturated or unsaturated, containing at least one heteroatom selected from nitrogen, oxygen, sulfur, silicon, selenium, phosphorus, optionally condensed with other aromatic or non-aromatic rings. Said heterocyclic groups can be optionally substituted with one or more groups, the same or different from each other, selected from: halogen atoms, such as, for example, fluorine, bromine, chlorine, preferably fluorine; hydroxyl groups; $C_1$-$C_{12}$ alkyl groups; $C_1$-$C_{12}$ alkoxyl groups; cyano groups; amino groups; nitro groups. Specific examples of heterocyclic groups are: pyrrolidine, methoxypyrrolidine, piperidine, fluoropiperidine, methylpiperidine, dihydropyridine, piperazine, morpholine, thiazine, induline, phenylindoline, 2-ketoazetidine, diketopiperazine, tetrahydrofuran, tetrahydrothiophene.

The term "cyclo" means a system containing a ring containing from 3 to 12 carbon atoms, optionally containing heteroatoms selected from nitrogen, oxygen, sulfur, silicon, selenium, phosphorus. Specific examples of cyclo are: toluene, benzonitrile, cycloheptatriene, cyclooctadiene, pyridine, thiadiazole, pyrrole, thiophene, selenophene, t-butylpyridine.

The term "trialkyl- or triaryl-silane groups" means silane groups containing three $C_1$-$C_{12}$ alkyl groups, or three $C_6$-$C_{12}$ aryl groups. Specific examples of trialkyl- or triaryl-silane groups are: trimethylsilane, triethylsilane, trihexylsilane, tridodecylsilane, dimethyldodecylsilane, triphenylsilane, methyldiphenylsilane, dimethylnaphthylsilane.

The term "dialkyl- or diaryl-amine groups" means amine groups containing two $C_1$-$C_{12}$ alkyl groups, or two $C_6$-$C_{12}$ aryl groups. Specific examples of dialkyl- or diaryl-amine groups are: dimethylamine, diethylamine, dibutylamine, diisobutylamine, diphenylamine, methylphenylamine, dibenzylamine, ditolylamine, dinaphthylamine.

The term "dialkyl- or diaryl-phosphine groups" means phosphine groups containing two $C_1$-$C_{12}$ alkyl groups, or two $C_6$-$C_{12}$ aryl groups. Specific examples of dialkyl- or diaryl-phosphine groups are: dimethylphosphine, diethylphosphine, dibutylphosphine, diphenylphosphine, methylphenylphosphine, dinaphthylphosphine.

The term "alkoxyl or aryloxyl groups" means groups having an oxygen atom attached to a $C_1$-$C_{12}$ alkyl group or to a $C_6$-$C_{12}$ aryl group. Specific examples of alkoxyl or aryloxyl groups are: methoxyl, ethoxyl, propoxyl, butoxyl, isobutoxyl, 2-ethylhexyloxyl, phenoxyl, benzyloxyl, naphthyloxyl.

The term "thioalkoxyl or thioaryloxyl groups" means groups having an oxygen atom and a sulfur atom attached to a $C_1$-$C_{12}$ alkyl group or to a $C_6$-$C_{12}$ aryl group. Specific examples of thioalkoxyl or thioaryloxyl groups are: thiomethoxyl, thioethoxyl, thiopropoxyl, thiobutoxyl, thioisobutoxyl, 2-ethylthiohexyloxyl, thiophenoxyl, thiobenzyloxyl.

Specific examples of compounds having general formula (I) are indicated in Table 1.

TABLE 1
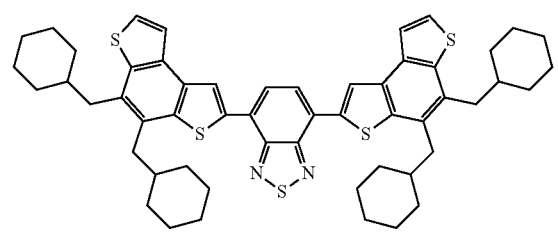 [SMILES: c1cc2c(s1)c(CC1CCCCC1)c(CC1CCCCC1)c1sc(-c3ccc(-c4cc5c(s4)c(CC4CCCCC4)c(CC4CCCCC4)c4sccc45)c4nsnc34)cc12]
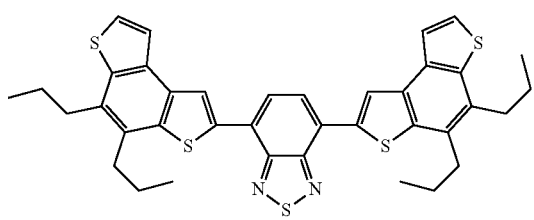 [SMILES: CCCc1c(CCC)c2sc(-c3ccc(-c4cc5c(s4)c(CCC)c(CCC)c4sccc45)c4nsnc34)cc2c2ccsc12]
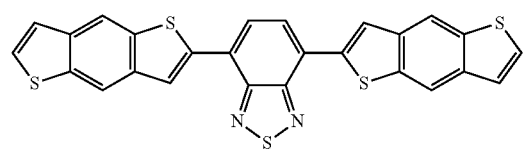 [SMILES: c1cc2cc3sc(-c4ccc(-c5cc6cc7sccc7cc6s5)c5nsnc45)cc3cc2s1]
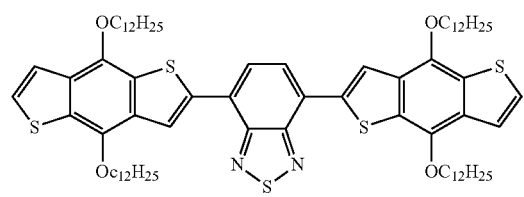
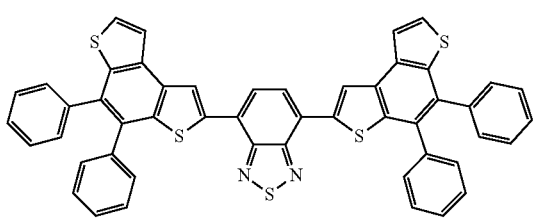 [SMILES: c1ccc(-c2c(-c3ccccc3)c3sc(-c4ccc(-c5cc6c(s5)c(-c5ccccc5)c(-c5ccccc5)c5sccc56)c5nsnc45)cc3c3ccsc23)cc1]
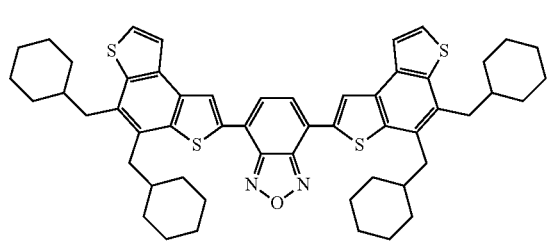 [SMILES: c1cc2c(s1)c(CC1CCCCC1)c(CC1CCCCC1)c1sc(-c3ccc(-c4cc5c(s4)c(CC4CCCCC4)c(CC4CCCCC4)c4sccc45)c4nonc34)cc12]
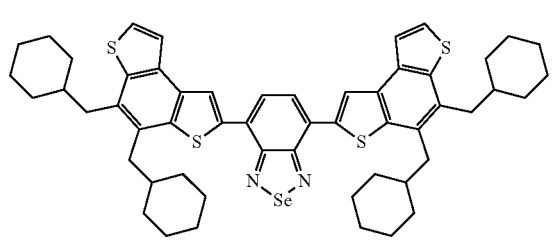 [SMILES: c1cc2c(s1)c(CC1CCCCC1)c(CC1CCCCC1)c1sc(-c3ccc(-c4cc5c(s4)c(CC4CCCCC4)c(CC4CCCCC4)c4sccc45)c4n[se]nc34)cc12]
TABLE 1-continued
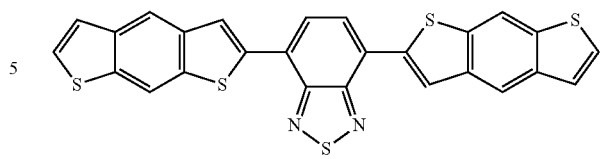
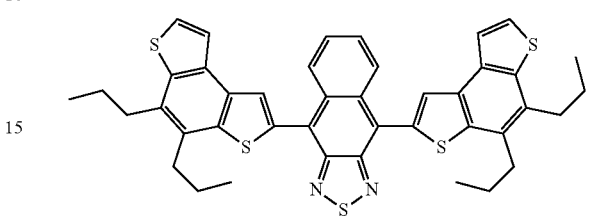
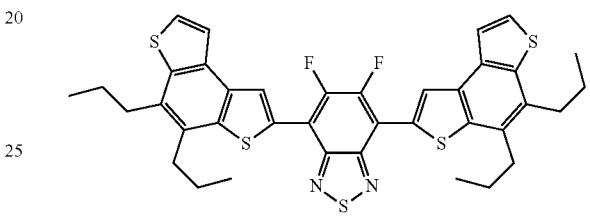
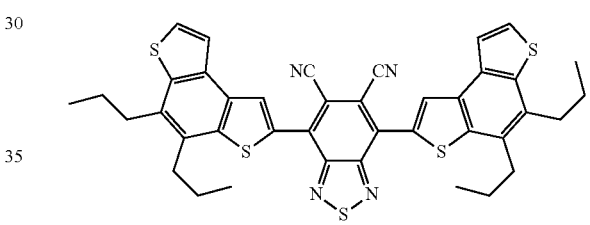
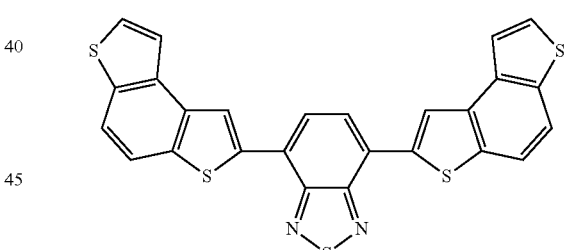
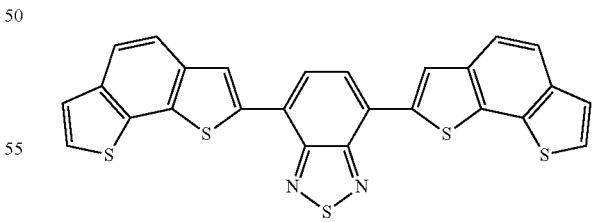
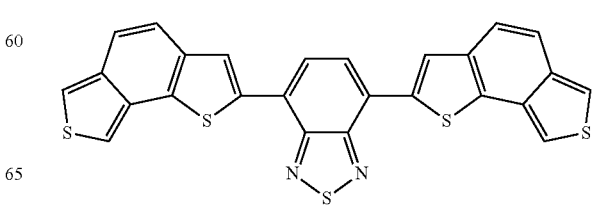

TABLE 1-continued
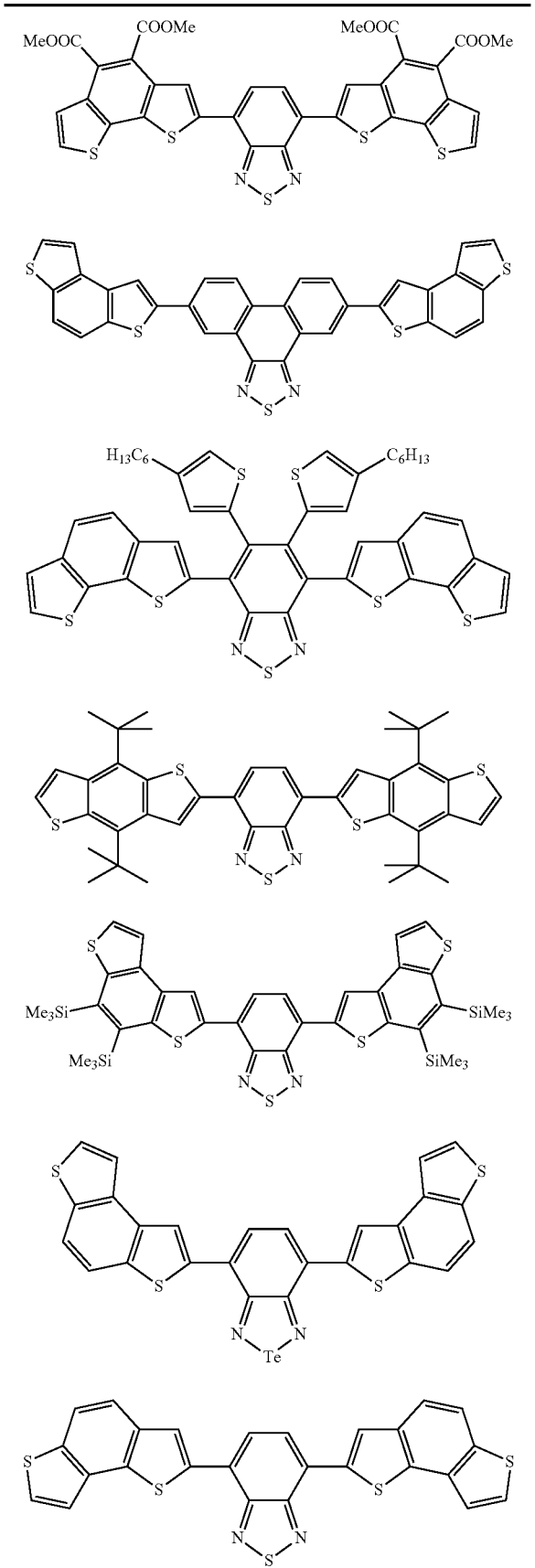

TABLE 1-continued
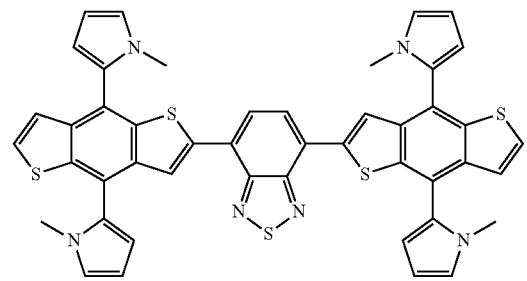 [SMILES: Cn1cccc1-c1c2cc(-c3ccc(-c4cc5c(-c6cccn6C)c6sccc6c(-c6cccn6C)c5s4)c4nsnc34)sc2c(-c2cccn2C)c2ccsc12]
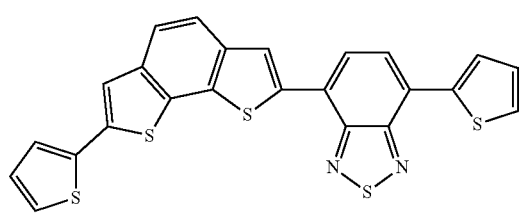 [SMILES: c1csc(-c2cc3ccc4cc(-c5ccc(-c6cccs6)c6nsnc56)sc4c3s2)c1]
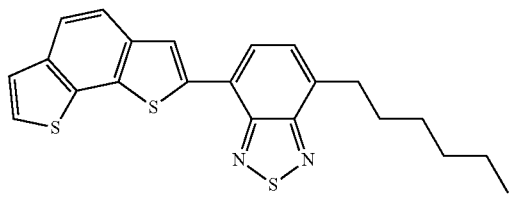 [SMILES: CCCCCCc1ccc(-c2cc3ccc4ccsc4c3s2)c2nsnc12]
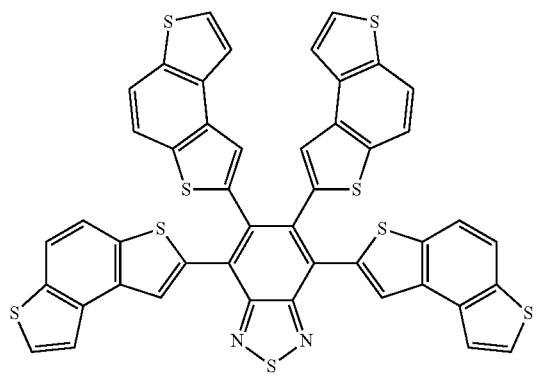 [SMILES: c1cc2c(ccc3sc(-c4c(-c5cc6c(ccc7sccc76)s5)c(-c5cc6c(ccc7sccc76)s5)c5nsnc5c4-c4cc5c(ccc6sccc65)s4)cc32)s1]
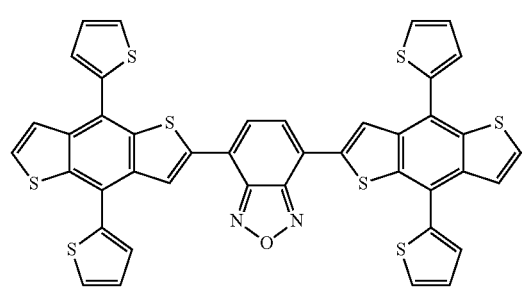 [SMILES: c1csc(-c2c3cc(-c4ccc(-c5cc6c(-c7cccs7)c7sccc7c(-c7cccs7)c6s5)c5nonc45)sc3c(-c3cccs3)c3ccsc23)c1]
TABLE 1-continued
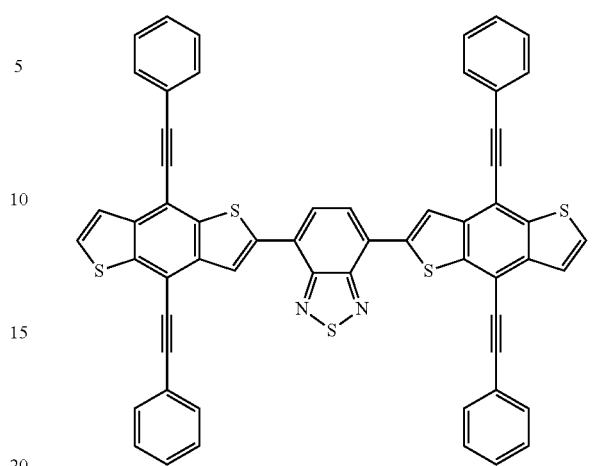
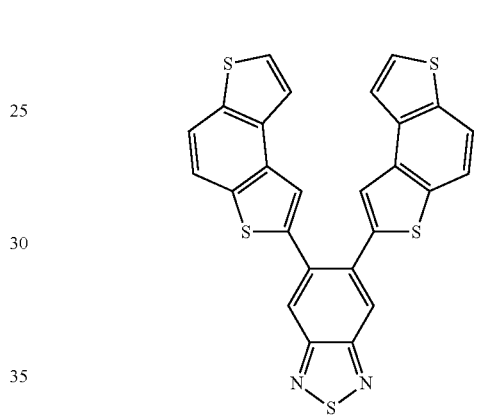
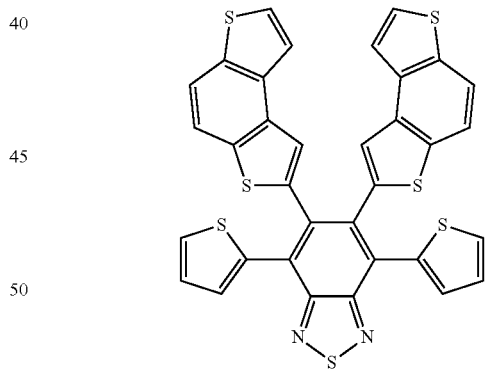
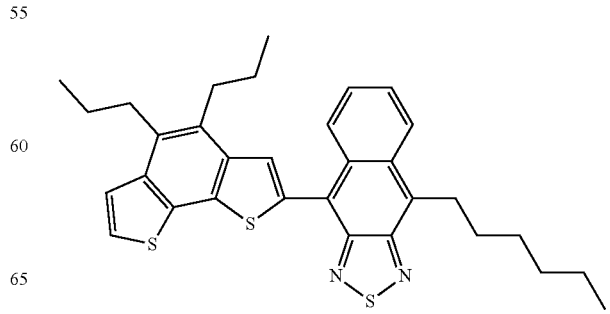

TABLE 1-continued

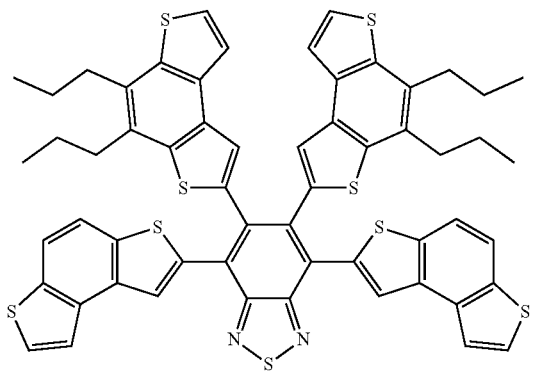 [SMILES: CCCc1c(CCC)c2sc(-c3c(-c4cc5c(s4)c(CCC)c(CCC)c4sccc45)c(-c4cc5c(ccc6sccc65)s4)c4nsnc4c3-c3cc4c(ccc5sccc54)s3)cc2c2ccsc12]

The compounds having general formula (I) object of the present invention can be obtained by means of various processes known in the art: further details relating to the preparation of the above compounds are provided in the following examples.

As described above, both said compound having general formula (I) and said mixture of compounds having general formula (I), can be advantageously used as spectrum converters in luminescent solar concentrators (LSCs), capable, in their turn, of enhancing the performances of solar devices such as, for example, photovoltaic cells, photoelectrolytic cells.

Said luminescent solar concentrators (LSCs) can be prepared, for example, by dispersion in the molten state of said compound having general formula (I), or said mixture of compounds having general formula (I), in polymeric materials such as, for example, polymethylmethacrylate (PMMA), polystyrene, polyvinyl acetate (PVA).

Consequently, a further object of the present invention relates to a luminescent solar concentrator (LSC) including at least one compound having general formula (I), or at least a mixture of compounds having general formula (I).

The luminescent solar concentrators (LSCs) object of the present invention can be produced in the form of prisms or of polymeric sheets to be coupled with solar devices. Alternatively, according to a different known constructive technique, the luminescent solar concentrators (LSCs) can be obtained by depositing a thin film laid on the surface of a sheet or of a transparent prism made of an organic or inorganic vitreous material such as, for example, glass, polymethylmethacrylate (PMMA).

A further object of the present invention relates to a solar device comprising a luminescent solar concentrator (LSC) including at least one compound having general formula (I) or at least a mixture of compounds having general formula (I).

Said solar device can typically include at least one photovoltaic cell or at least one photoelectrolytic cell, positioned on the edges of a sheet comprising at least one compound having general formula (I) or at least a mixture of compounds having general formula (I).

Some illustrative and non-limiting examples are provided hereunder for a better understanding of the present invention and for an embodiment of the same.

In the following examples, the analytical techniques and characterization methods listed below, were used.

NMR Spectra

The NMR spectra of the compounds obtained were acquired by means of a NMR Bruker Avance 400 spectrometer.

For this purpose, about 10 mg of the sample to be examined were dissolved in about 0.8 ml of an appropriate deuterated solvent directly in the glass tube used for the measurement. The scale of the chemical shifts was calibrated with respect to the tetramethylsilane signal, fixed at 0 ppm.

Mass Spectra

The mass spectra of the compounds obtained were carried out with an inverse-geometry double-focusing spectrometer AT 95S in DCI ("Desorption Chemical Ionization") with iso-butane as reagent gas in positive ion modality. The emission current of the filament was calibrated at 0.1 mA with an electron beam energy equal to 100 eV and with a temperature of the ion source maintained at 90° C.

Absorption Spectra

The absorption spectra of the solutions in methylene chloride ($CH_2Cl_2$) of the compounds having general formula (I) obtained or of the polymethylmethacrylate films containing the compounds having general formula (I) obtained, in the ultraviolet and visible range (UV-Vis) (250 nm-800 nm), were acquired through the transmission technique, using a Perkin Elmer λ 950 double-beam and double-monochromator spectrophotometer, with a bandwidth of 2.0 nm and step of 1.0 nm. The ideal wavelength (generally λ=490 nm–510 nm) was defined from said spectra for the subsequent photoluminescence measurements, in correspondence with the maximum absorption area of the compound having general formula (I) examined.

Molar Extinction Coefficient (ε)

The molar extinction coefficient (ε) in a solution of methylene chloride ($CH_2Cl_2$) of the compounds having general formula (I) obtained, was obtained as follows.

At least 5 solutions with a known titre for each compound having general formula (I) were prepared for the purpose: the UV-visible absorption spectrum was then registered for each solution and, maintaining an optical path of 1 cm, the relative absorbance value was read at the spectral position of the maximum value of the absorption band under examination.

The calculation of the molar extinction coefficient (ε) was then carried out using the Lambert-Beer law ($A=\varepsilon bc$ wherein ε is the molar extinction coefficient, b is the optical path, c is the molar concentration, A is the absorbance) according to what is described by N. J. Turro, V. Ramamurthy and J. C. Scaiano in "Modern Molecular Photochemistry of Organic Molecules" (2010), ISBN 978-1-891389-25-2, pages 215-217.

Emission Spectra

The emission spectra of the solutions in methylene chloride ($CH_2Cl_2$) of the compounds having general formula (I) obtained, or of the polymethylmethacrylate films containing the compounds having general formula (I) obtained, were registered using a Horiba Jobin Yvon Fluorolog 3 spectrofluorimeter, operating in a "front-face" configuration and exciting at the wavelength selected as described above (i.e. ideal wavelength).

Stokes Shift

The Stokes Shift was obtained from an analysis of the absorption and emission spectra for each compound having general formula (I) obtained, and was calculated as the difference, in frequency units ($cm^{-1}$), between the spectral positions of the maximum values of the absorption band and of the emission band.

Determination of the Luminescence Quantum Efficiency (Φ)

The luminescence quantum efficiency (Φ) of the solutions in methylene chloride ($CH_2Cl_2$) of the compounds having general formula (I) obtained, was obtained indirectly using a standard having a known luminescence quantum efficiency (Φ), according to what is described by A. T. R. Williams, S. A. Winfield and J. N. Miller in "Analyst" (1983), Vol. 108, page 1067.

Rhodamina 101 dissolved in ethyl alcohol was used for the purpose, as reference standard, and the calculation method described by M. Montali et al. in "Handbook of Photochemistry" (2006), Taylor & Francis Group, pages 572-576, was adopted.

Thickness of the Polymethylmethacrylate Films

The measurements of the thickness of the polymethylmethacrylate films were obtained using a gauge in twentieths.

Reagents and Materials

The following reagents and materials were used during the preparations described in the examples:

tetrahydrofuran (THF) of Aldrich;
tetramethylethylenediamine (TMEDA) of Aldrich;
lithium-n-butyl of Aldrich;
methylene chloride ($CH_2Cl_2$) of Acros;
sodium sulfate ($Na_2SO_4$) of Acros;
hexane of Carlo Erba;
ethyl acetate of Acros;
deuterated chloroform ($CDCl_3$) of Carlo Erba;
palladium-tetrakistriphenylphosphine [$Pd(PPh_3)_4$] of Aldrich;
4,7-dibromobenzo[c][1,2,5]thiodiazole of Aldrich;
toluene of Carlo Erba;
potassium carbonate ($K_2CO_3$) of Carlo Erba;
methanol (MeOH) of Carlo Erba;
acetone of Carlo Erba;
deuterated methylene chloride ($CD_2Cl_2$) of Carlo Erba;
titanium tetrachloride ($TiCl_4$) of Aldrich;
zinc (Zn) in powder form of Aldrich;
hydrochloric acid (HCl) of Carlo Erba;
iodine ($I_2$) of Acros;
ammonium chloride ($NH_4Cl$) of Carlo Erba;
ethanol of Carlo Erba;
ethyl ether of Carlo Erba;
acetonitrile of Aldrich;
2-isopropoxy-4,4,5,5-tetramethyl-1,3,2-dioxaborolane of Aldrich
4,7-bis-[2-(4,4,5,5-tetramethyl-1,3,2-dioxaborolan-2-yl)][c][1,2,5]thiodiazole of Aldrich;
7,8-dicyclohexylmethylbenzo[1,2-b:4,3-b']dithiophene: prepared according to what is reported by Rigamonti, C. et al. in "Heterocycles" (2008), Vol. 76, pages 1439-1470;
1-(2-thienyl)-butan-1-one: prepared according to what is reported by Sundby E. et al. in "Arkivoc" (2001), Vol. (x), pages 76-84;
2-(4,4,5,5-tetramethyl-1,3,2-dioxoborolan-2-yl)-, 4,8-di-dodecyloxybenzo-[1,2-b:4,5-b']dithiophene: prepared according to the same synthesis process as 2-(4,4,5,5-tetramethyl-1,3,2-dioxoborolan-2-yl)-7,8-dicyclohexylmethylbenzo-[1,2-b:4,3-b']dithiophene having formula (2) described in Example 1 provided hereunder.

The commercial compounds were generally used in the following examples as received from the supplier. When necessary, the solvents used were anhydrified, operating according to the methods known in the art.

Example 1

Preparation of 4,7-bis(7,8-dicyclohexylmethylbenzo[1,2-b:4,3-b']dithiophene)benzo[c][1,2,5]thiadiazole having formula (3)

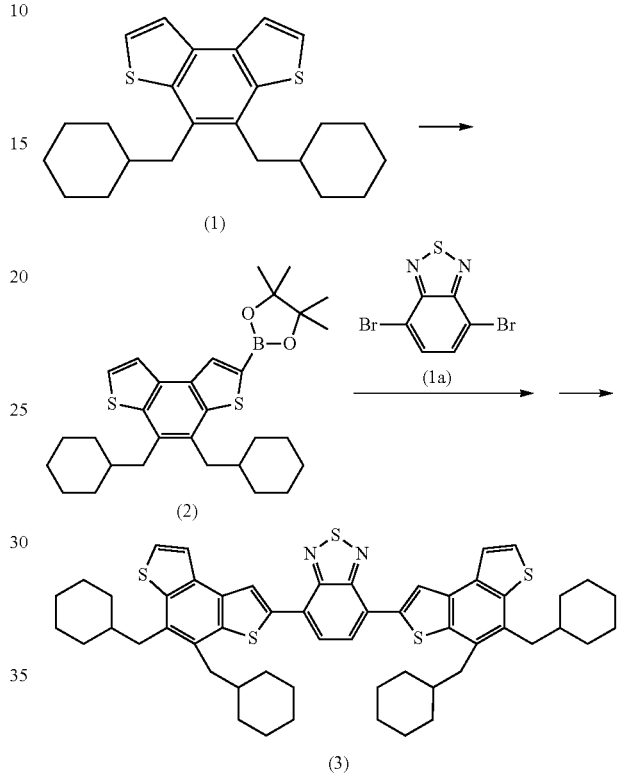

The following products were introduced, in order, into a 100 ml sidearm round-bottom flask containing 30 ml of anhydrous tetrahydrofuran (THF): 0.26 g (0.68 mmoles) of 7,8-dicyclohexylmethylbenzo[1,2-b:4,3-b']dithiophene having formula (1). The solution thus obtained was cooled to −78° C. and the following products were then introduced in order: 0.21 ml (1.37 mmoles) of tetramethylethylenediamine (TMEDA) and 1.0 ml of a 1.6 M solution of lithium n-butyl in hexane (1.6 mmoles). The yellow-coloured reaction mixture was kept under stirring, for 30 minutes, at −78° C., after which 0.7 ml of 2-isopropoxy-4,4,5,5-tetramethyl-1,3,2-dioxaborolane (3.43 mmoles) dissolved in 5 ml of anhydrous tetrahydrofuran (THF) were added, by means of a drip funnel, over a period of about 10 minutes. The reaction mixture was slowly brought to 25° C., kept under stirring for a further 2 hours and then treated with 30 ml of water. After extraction with methylene chloride (3×30 ml), the organic phase obtained was washed with water (2×10 ml) and finally treated with anhydrous sodium sulfate ($Na_2SO_4$) to eliminate traces of humidity. Finally, after removing the solvent at reduced pressure, an oily brown-coloured product was obtained, which was purified by chromatography on a neutral alumina column using hexane as eluent and subsequently a mixture of hexane/ethyl acetate (70/30 vol/vol), obtaining 0.3 g (yield 87%) of 2-(4,4,5,5-tetramethyl-1,3,2-dioxoborolan-2-yl)-7,8-dicyclohexylmethylbenzo[1,2-b:4,3-b']dithiophene having formula (2).

Said compound having formula (2) was characterized by means of $^1$H-NMR ($CDCl_3$, 300 MHz) obtaining the following spectrum: δ 1.04-1.20 (m, 12H); 1.39 (s, 12H); 1.50-1.93 (m, 10H); 2.89 (d, 2H, J=3.6 Hz); 2.91 (d, 2H, J=3.6 Hz); 7.45 (d, 1H, J=6.0 Hz); 7.67 (d, 1H, J=6.0 Hz); 8.22 (s, 1H).

Said compound having formula (2) was also characterized by means of $^{13}$C-NMR (CDCl$_3$, 75 MHz) obtaining the following spectrum: δ 24.8 (CH$_3$); 26.5 (CH$_2$); 33.8 (CH$_2$); 38.6 (CH); 38.9 (CH); 40.1 (CH$_2$); 40.2 (CH$_2$); 85.5 (Cq); 122.5 (CH); 125.2 (CH); 129.9 (Cq); 131.6 (Cq); 132.7 (CH), 133.1 (Cq) 133.7 (Cq) 138.9 (Cq); 143.5 (Cq).

Finally, said compound having formula (2) was characterized by means of MS-EI (m/z) mass spectrum, obtaining the following value: [M$^+$]: 508; calculated for C$_{30}$H$_{41}$BO$_2$S$_2$: 508.586.

The following products were introduced, in order, in an inert atmosphere, into a 50 ml sidearm round-bottom flask: 8 mg (0.007 mmoles) of palladium-tetrakistriphenylphosphine [Pd(PPh$_3$)$_4$], 0.056 g (0.19 mmoles) of 4,7-dibromobenzo[c][1,2,5]thiodiazole, 0.3 g (0.59 mmoles) of 2-(4,4,5,5-tetramethyl-1,3,2-dioxoborolan-2-yl)-7,8-dicyclohexylmethyl-benzo[1,2-b:4,3-b']dithiophene having formula (2) obtained as described above, 15 ml of toluene and 7 ml of a 2 M aqueous solution of potassium carbonate (K$_2$CO$_3$). The reaction mixture was then heated to the reflux temperature of the solvent for 2 hours: in this phase, the mixture becomes deep red-coloured. After cooling the mixture to 25° C. and removing the solvent at reduced pressure, an oily red residue is obtained which is purified by chromatography on a silica gel column using a mixture of hexane/methylene chloride (CH$_2$Cl$_2$) as eluent (1/1 vol/vol). The solid red residue obtained was subsequently washed with methanol (2×10 ml) and acetone (2×10 ml) and dried under vacuum, for 4 hours, at 25° C., obtaining 0.085 g (yield 49%) of 4,7-bis(7,8-dicyclohexylmethylbenzo[1,2-b:4,3-b']dithiophene)benzo[c][1,2,5]thiadiazole having formula (3) as a red microcrystalline solid.

Said compound having formula (3) was characterized by means of $^1$H-NMR (CDCl$_3$, 300 MHz) obtaining the following spectrum: δ 1.08-1.26 (m, 24H); 1.55-1.98 (m, 20H); 2.97-3.03 (m, 8H); 7.52 (d, 2H, J=5.4 Hz); 7.84 (d, 2H, J=5.4 Hz); 8.05 (s, 2H); 8.92 (s, 2H).

Said compound having formula (3) was also characterized by means of $^{13}$C-NMR (CDCl$_3$, 75 MHz) obtaining the following spectrum: δ 26.5 (CH$_2$); 33.9 (CH$_2$); 38.9 (CH); 39.0 (CH); 40.1 (CH$_2$); 40.3 (CH$_2$); 122.6 (CH); 124.0 (CH); 125.2 (CH); 126.5 (C$_q$); 126.7 (CH); 131.1 (C$_q$); 133.0 (C$_q$); 133.7 (C$_q$); 137.9 (C$_q$); 139.3 (C$_q$); 139.6 (C$_q$); 152.9 (C$_q$).

Finally, said compound having formula (3) was characterized by means of MS-EI (m/z) mass spectrum, obtaining the following value: [M$^+$]: 897; calculated for C$_{54}$H$_{60}$N$_2$S$_5$: 897.393.

Example 2

Preparation of 4,7-bis(4,8-didodecyloxybenzo[1,2-b:4,5-b']dithiophene)benzo[c][1,2,5]thiadiazole having formula (5)

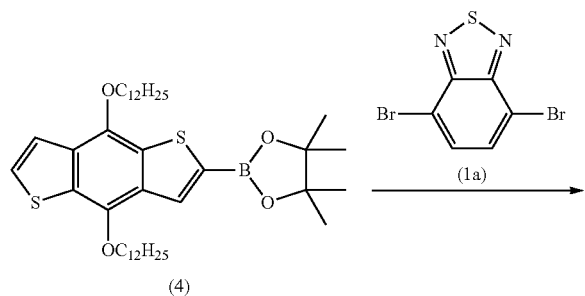

(4)

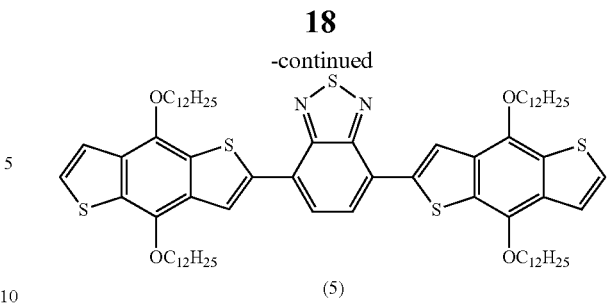

(5)

The following products were introduced, in order, in an inert atmosphere, into a 50 ml sidearm round-bottom flask: 4 mg (0.003 mmoles) of palladium-tetrakistriphenylphosphine [Pd(PPh$_3$)$_4$], 0.040 g (0.14 mmoles) of 4,7-dibromobenzo[c][1,2,5]thiodiazole having formula (1a), 0.3 g (0.44 mmoles) of 2-(4,4,5,5-tetramethyl-1,3,2-dioxoborolan-2-yl)-4,8-didodecyloxybenzo[1,2-b:4,5-b']-dithiophene having formula (4), 15 ml of toluene and 4 ml of a 2 M aqueous solution of potassium carbonate (K$_2$CO$_3$). The reaction mixture was then heated to the reflux temperature of the solvent for 2 hours: in this phase, the mixture becomes deep red-coloured. After cooling the mixture to 25° C. and removing the solvent at reduced pressure, a red oily residue is obtained which is purified by chromatography on a silica gel column using a mixture of hexane/methylene chloride (CH$_2$Cl$_2$) as eluent (2/1 vol/vol). The dark-red oily residue obtained was recovered, washed with methanol (2×20 ml) and subsequently with acetone (3×20 ml). After drying at reduced pressure for 6 hours, at 25° C., 0.030 g (yield 17%) of 4,7-bis(4,8-didodecyloxybenzo[1,2-b:4,5-b']dithiophene)benzo[c][1,2,5]thiadiazole having formula (5) were obtained as a dark-red-purple microcrystalline solid.

Said compound having formula (5) was characterized by means of $^1$H-NMR (CD$_2$Cl$_2$, 400 MHz) obtaining the following spectrum: δ 0.78-0.91 (m, 12H); 1.12-1.68 (m, 72H); 1.69-1.91 (m, 8H); 4.33 (t, 4H, J=8 Hz); 4.4 (t, 4H, J=8 Hz); 7.43 (d, 2H J=8 Hz); 7.5 (d, 2H, J=8 Hz); 8.05 (s, 2H); 8.83 (s, 2H).

Said compound having formula (5) was also characterized by means of $^{13}$C-NMR (CDCl$_3$, 75.5 MHz) obtaining the following spectrum: δ 13.4 (CH$_3$); 22.5 (CH$_2$); 25.1 (CH$_2$); 25.4 (CH$_2$); 28.3-29.5 (CH$_2$); 30.7 (CH$_2$); 31.3 (CH$_2$); 74.4 (CH$_2$); 74.1 (CH$_2$); 121.8 (CH); 123.6 (CH); 127.8 (CH); 128.3 (CH); 133.3 (C$_q$); 133.7 (C$_q$); 139.1 (C$_q$); 144.5 (C$_q$); 145.5 (C$_q$); 152.9 (C$_q$).

Finally, said compound having formula (5) was characterized by means of MS-EI (m/z) mass spectrum, obtaining the following value: [M$^+$]: 1248; calculated for C$_{74}$H$_{108}$N$_2$O$_4$S$_5$: 1249.98.

Example 3

Preparation of 4,7-bis(7,8-di-n-propyl-benzo[1,2-b:4,3-b']dithiophene)benzo[c][1,2,5]thiadiazole having formula (10)

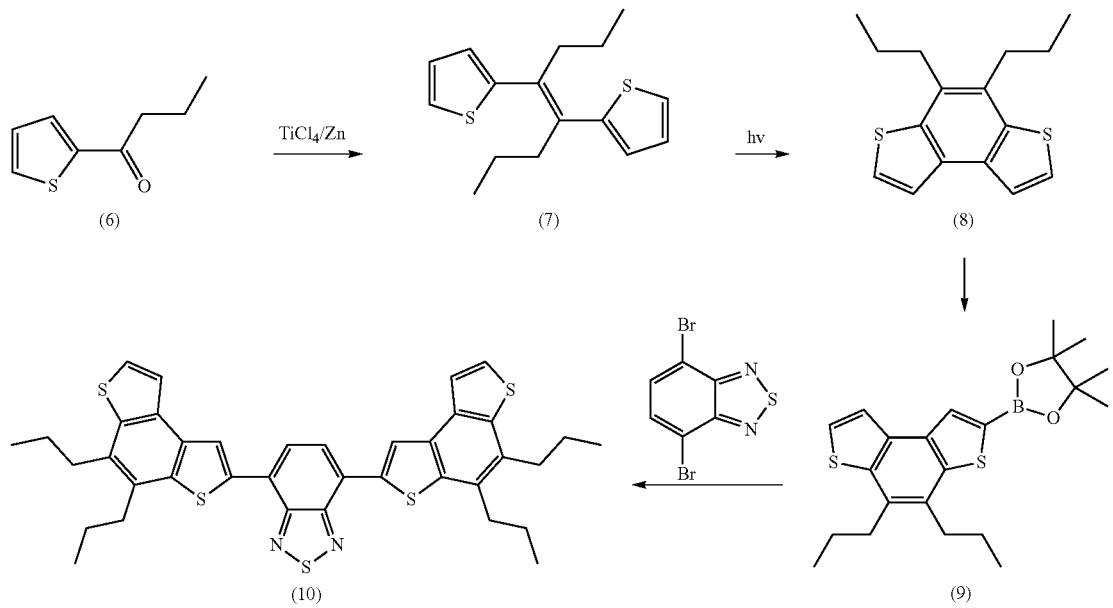

The following products were introduced, in order, in an inert atmosphere, into a 100 ml sidearm round-bottom flask: 4.0 g (25.9 mmoles) of 1-(2-thienyl)butan-1-one having formula (6) and 60 ml of anhydrous tetrahydrofuran (THF). After cooling the reaction mixture to −30° C., 3.4 ml (31.1 mmoles) of titanium chloride (TiCl$_4$) were slowly added, by means of a syringe, obtaining a yellow solution to which 4.23 g (64 mmoles) of zinc (Zn) powder were added. The reaction mixture was kept under stirring, for 30 minutes, was then left to heat slowly to 25° C. and was finally heated to the reflux temperature of the solvent for 4 hours. After cooling to 25° C., the reaction mixture was treated, at 0° C., with an 0.5 M aqueous solution of hydrochloric acid (HCl) and extracted with methylene chloride (CH$_2$Cl$_2$) (3×100 ml). The organic phase obtained was washed with water (2×20 ml) and finally treated with anhydrous sodium sulfate (Na$_2$SO$_4$) to eliminate traces of humidity. After removing the solvent at reduced pressure, a solid raw product was obtained, which was purified by chromatography on a silica gel column using hexane as eluent, obtaining 2.97 g (83% yield) of 4,5-bis(2-thienyl)oct-4-ene having formula (7).

Said compound having formula (7) was characterized by means of $^1$H-NMR (CDCl$_3$, 300 MHz) obtaining the following spectrum: δ 0.94 (t, 6H, J=7.35 Hz, CH$_3$); 1.45 (m, 4H, CH$_2$CH$_3$); 2.53 (t, 4H, J=7.8 Hz, CCH$_2$); 6.71 (d, 2H, J=3.6 Hz); 6.84 (dd, 2H,); 7.13 (d, 2H, J=5.1 Hz).

Said compound having formula (7) was also characterized by means of $^{13}$C-NMR (CDCl$_3$, 75 MHz) obtaining the following spectrum: δ 14.06; 21.84; 37.65; 76.64; 77.07; 77.49; 124.89; 126.34; 126.49; 133.03; 145.09.

Finally, said compound having formula (7) was characterized by means of MS-EI (m/z) mass spectrum, obtaining the following values: 276; [M-C$_2$H$_5$$^+$]: 247 and HR-MS (EI) obtaining [M$^+$]: 276.09484, calculated for C$_{16}$H$_{20}$S$_2$: 276.10064.

2.7 g (9.8 mmoles) of 4,5-bis(2-thienyl)oct-4-ene having formula (7) obtained as described above, 750 ml of toluene and 0.03 g (0.12 mmoles) of iodine (I$_2$) were introduced into a 1 liter photoreactor, equipped with a 150 W medium-pressure mercury lamp. The solution thus obtained was irradiated for 6 hours and during this period air was bubbled into the solution through a cannula. The reaction mixture obtained was then washed with an 0.5 M solution of sodium sulfate (Na$_2$SO$_3$) (3×100 ml) and then with water (3×100 ml) and the solvent removed at reduced pressure. The raw product obtained was purified by chromatography on a silica gel column using hexane as eluent, obtaining 2.4 g (89% yield) of 7,8-di-n-propyl-benzo[1,2-b:4,3-b']dithiophene having formula (8) as a colourless microcrystalline solid.

Said compound having formula (8) was characterized by means of $^1$H-NMR (CDCl$_3$, 300 MHz) obtaining the following spectrum: δ 1.09 (t, 6H, J=7.35 Hz, CH$_3$); 1.78 (m, 4H, CH$_2$CH$_3$); 2.99 (t, 4H, J=8.0 Hz, CCH$_2$); 7.46 (d, 2H, J=5.4 Hz); 7.67 (d, 2H, J=5.4 Hz).

Said compound having formula (8) was also characterized by means of $^{13}$C-NMR (CDCl$_3$, 75 MHz) obtaining the following spectrum: δ 17.75; 23.23; 34.45; 76.69; 77.11; 77.54; 122.48; 124.97; 130.25; 132.81; 138.81.

Finally, said compound having formula (8) was characterized by means of MS-EI (m/z) mass spectrum, obtaining the following values: 274; [M-C$_2$H$_5$$^+$]: 245 and HR-MS (EI) obtaining [M$^+$]: 274.08316, calculated for C$_{16}$H$_{18}$S$_2$: 274.08499.

The following products were introduced, in order, in an inert atmosphere, into a 100 ml sidearm round-bottom flask: 2.0 g (7.3 mmoles) of 7,8-di-n-propyl-benzo[1,2-b:4,3-b']dithiophene having formula (8) obtained as described above, 50 ml of anhydrous tetrahydrofuran (THF), and, after cooling the resulting solution to −78° C., 4.9 ml of a 1.6 M solution of lithium n-butyl in hexane (7.8 mmoles). The reaction mixture was kept under stirring at −78° C., for 20 minutes, slowly heated to 25° C. and kept under stirring at this temperature for a further 20 minutes. The yellow-coloured solution obtained was cooled again to −78° C., and 1.6 ml of 2-isopropoxy-4,4,5,5-tetramethyl-1,3,2-dioxaborolane (8.1 mmoles) dissolved in 10 ml of anhydrous tetrahydrofuran (THF) were subsequently added by means of a drip funnel, over a period of 10 minutes. The reaction mixture was slowly brought to 25° C., kept under stirring for a further 2 hours and then treated with 30 ml of a saturated aqueous solution of ammonium chloride ($NH_4Cl$). After extraction with ethyl acetate (3×30 ml), the organic phase obtained was washed with water (2×10 ml) and finally treated with anhydrous sodium sulfate ($Na_2SO_3$) to eliminate traces of humidity. After removing the solvent at reduced pressure, an oily bluish-coloured raw product was obtained, which was purified by chromatography on a neutral alumina column using hexane as eluent and subsequently a mixture of hexane/ethyl acetate (80/20 vol/vol), obtaining 2.7 g (93% yield) of 2-(4,4,5,5-tetramethyl-1,3,2-dioxoborolan-2-yl)-7,8-di-n-propyl-benzo[1,2-b:4,3-b']dithiophene having formula (9).

Said compound having formula (9) was characterized by means of $^1$H-NMR ($CDCl_3$, 300 MHz) obtaining the following spectrum: δ 1.08 (t, 3H, J=7.4 Hz); 1.09 (t, 3H, J=7.4 Hz); 1.72-1.85 (m, 4H); 2.94-3.03 (m, 4H); 7.47 (d, 1H, J=5.4 Hz); 7.68 (d, 1H, J=5.4 Hz); 8.23 (s, 1H).

The following products were introduced, in order, in an inert atmosphere, into a 50 ml sidearm round-bottom flask: 8 mg (0.007 mmoles) of palladium-tetrakistriphenylphosphine [$Pd(PPh_3)_4$], 0.25 g (0.8 mmoles) of 4,7-dibromobenzo[c][1,2,5]thiodiazole having formula (1a), 8 ml of degassed toluene, a solution of 1.0 g (2.5 mmoles) of 2-(4,4,5,5-tetramethyl-1,3,2-dioxoborolan-2-yl)-7,8-di-n-propyl-benzo[1,2-b:4,3-b']dithiophene having formula (9) obtained as described above, in 2 ml of ethanol and 4 ml of a 2 M aqueous solution of potassium carbonate ($K_2CO_3$)). The reaction mixture was then heated to the reflux temperature of the solvent for 7 hours, subsequently cooled to 25° C. and transferred to a separator funnel where the aqueous phase was separated from the organic phase. The organic phase obtained was washed with water (2×10 ml), whereas the aqueous phase was extracted with methylene chloride ($CH_2Cl_2$) (2×30 ml) obtaining extracts which were joined with the organic phase obtained from the washing with water: the whole mixture was treated with anhydrous sodium sulfate ($Na_2SO_4$) to eliminate traces of humidity. After removing the solvent at reduced pressure, a dark red-coloured raw residue was obtained, which was crystallized from ethyl ether/hexane. The solid obtained from the crystallization was treated with methylene chloride ($CH_2Cl_2$) and the soluble part was further purified by chromatography on a silica gel column using hexane/methylene chloride ($CH_2Cl_2$) as eluent (70/30, vol/vol), obtaining 0.08 g (15% yield) of 4,7-bis(7,8-di-n-propyl-benzo[1,2-b:4,3-b']dithiophene)benzo[c][1,2,5]thiadiazole having formula (10).

Said compound having formula (10) was characterized by means of $^1$H-NMR ($CDCl_3$, 300 MHz) obtaining the following spectrum: δ 1.10-1.21 (m, 12H); 1.79-1.91 (m, 8H); 2.99-3.07 (m, 8H); 7.51 (d, 2H, J=5.4 Hz); 7.81 (d, 2H, J=5.4 Hz); 7.98 (s, 2H); 8.88 (s, 2H).

Finally, said compound having formula (10) was characterized by means of MS (ESI$^+$) (m/z) mass spectrum, obtaining the following value: [M+H$^+$]: 681.1; calculated for $C_{38}H_{36}N_2S_5$: 681.02.

Example 4

Preparation of 4,7-bis(benzo[1,2-b:4,5-b']dithiophene)benzo[c][1,2,5]thiadiazole having formula (13)

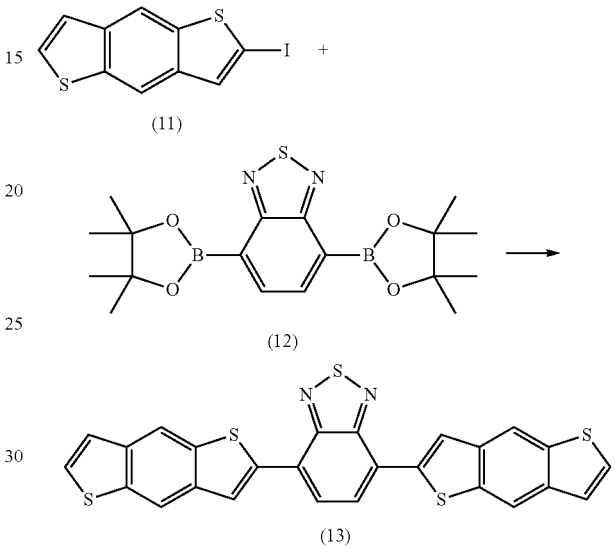

The following products were introduced, in order, in an inert atmosphere, into a 25 ml sidearm round-bottom flask: 0.052 g (0.16 mmoles) of 2-iodo-benzo[1,2-b:4,5-b']dithiophene having formula (11), 0.030 g (0.08 mmoles) of 4,7-bis-[2-(4,4,5,5-tetramethyl-1,3,2-dioxoborolan-2-yl)][c][1,2,5]thiodiazole having formula (12), 1.6 ml of a 2 M aqueous solution of potassium carbonate ($K_2CO_3$), 10 ml of toluene and 9 mg (0.008 mmoles) of palladium-tetrakistriphenylphosphine [$Pd(PPh_3)_4$]. The reaction mixture was then heated to the reflux temperature of the solvent for 24 hours obtaining a dark red suspension. After cooling to 25° C., the reaction mixture was transferred to a 250 ml flask containing 100 ml of methylene chloride ($CH_2Cl_2$) and washed with water (3×10 ml): the organic phase obtained was treated with anhydrous sodium sulfate ($Na_2SO_9$) to eliminate traces of humidity. After removing the solvent at reduced pressure, a dark red-coloured raw residue was obtained, which was purified through washings with hexane, ethyl ether, acetonitrile and finally with a mixture of hexane/methylene chloride ($CH_2Cl_2$) (1/1, vol/vol) obtaining 0.017 g (41% yield) of 4,7-bis(benzo[1,2-b:4,5-b']dithiophene)benzo[c][1,2,5]thiadiazole having formula (13).

Said compound having formula (13) was characterized by means of $^1$H-NMR ($CDCl_3$, 300 MHz) obtaining the following spectrum: δ 7.38 (d, 2H, J=5.5 Hz); 7.50 (d, 2H, J=5.5 Hz); 8.01 (s, 2H); 8.31 (s, 2H); 8.40 (s, 2H); 8.70 (s, 2H).

Finally, said compound having formula (13) was characterized by means of MS (ESI$^+$) (m/z) mass spectrum, obtaining the following value: [M+H$^+$]: 513.7; calculated for $C_{26}H_{12}N_2S_5$: 512.69.

Example 5

Preparation of a polymethylmethacrylate (PMMA) film containing 4,7-bis(7,8-dicyclohexylmethylbenzo[1,2-b:4,3-b']dithiophene)benzo[c][1,2,5]thiadiazole having formula (3) for measuring the spectroscopic properties The measurement of the spectroscopic properties of 4,7-bis(7,8-dicyclohexylmethylbenzo[1,2-b:4,3-b']dithiophene)benzo[c][1,2,5]thiadiazole having formula (3), obtained according to what is described in Example 1, was carried out by the dispersion of said compound in a polymethylmethacrylate matrix [(PMMA) of Aldrich, Mw=350,000].

For this purpose, 0.275 g of polymethylmethacrylate (PMMA), 1 ml of chloroform ($CHCl_3$) and 0.1 ml of a solution obtained by dissolving 1.5 mg ($1.7 \times 10^{-3}$ mmoles) of 4,7-bis(7,8-dicyclohexylmethylbenzo[1,2-b:4,3-b']dithiophene)benzo[c][1,2,5]thiadiazole having formula (3) in 1.5 ml of chloroform ($CHCl_3$) were introduced into a 5 ml flask. The mixture obtained was kept in movement, at 25° C., by means of a shaker, for 16 hours, until the complete dissolution of the polymethylmethacrylate (PMMA).

A part of the solution thus obtained was then deposited on a quartz plate (2 cm×2 cm) with optical surfaces, maintained in a perfectly horizontal position. The plate was then covered with a suitably sized beaker, so as to form an environment almost saturated with chloroform ($CHCl_3$) thus obtaining a slow evaporation of the chloroform ($CHCl_3$) to prevent the formation of microbubbles inside the film.

Once the solvent had completely evaporated (3 days), the polymethylmethacrylate (PMMA) film containing 4,7-bis(7,8-dicyclohexylmethylbenzo[1,2-b:4,3-b']dithiophene)benzo[c][1,2,5]thiadiazole having formula (3) was detached from the quartz support.

The film obtained had a thickness (determined by operating as described above) of 433 μm and contained $4.12 \times 10^{-4}$ mmoles of compound (3) per g of polymethylmethacrylate (PMMA).

The absorption spectrum, emission spectrum, Stokes shift and thickness were acquired on the film thus obtained, operating as described above: the values obtained are indicated in Table 2.

Examples 6-8

Preparation of a Polymethylmethacrylate (PMMA) Film Containing Compounds Having General Formula (I) for Measuring the Spectroscopic Properties According to the procedure described in Example 5, polymethylmethacrylate (PMMA) films were prepared, containing compounds having formula (5), formula (10) and formula (13), prepared according to what is described in Examples 2, 3 and 4, respectively.

The absorption spectrum, emission spectrum, Stokes shift and thickness were acquired on each film thus obtained, operating as described above: the values obtained are indicated in Table 2.

Table 2 indicates, in order: the Example number (Example), the number referring to the formula of the compound used (Formula compound), the number of the example in which the compound was prepared (Example prep.), the concentration of compound in the film (C) expressed as mmoles of compound per gram of polymer (mmoles/g pol.), the thickness of the film in μm (Thickness), the value of the maximum of the lowest energy band in the absorption spectrum [$\lambda_{max}$ (ass.)] expressed in (nm) and in [$cm^{-1}$], the value of the maximum of the highest energy band in the emission spectrum [$\lambda_{max}$ (emiss.)] expressed in (nm) and in [$cm^{-1}$], and finally the Stokes shift value expressed in ($cm^{-1}$).

TABLE 2

| Ex. | Formula compound | Example Prep. | C (mmoli/g pol.) | Thickness (μm) | $\lambda_{max}$ (ads.) (nm) [$cm^{-1}$] | $\lambda_{ma}$ (emiss.) (nm) [$cm^{-1}$] | Stokes shift ($cm^{-1}$) |
|---|---|---|---|---|---|---|---|
| 5 | (3) | 1 | $4.1 \times 10^{-4}$ | 433 | 495 [20202] | 586 [17065] | 3137 |
| 6 | (5) | 2 | $3.2 \times 10^{-4}$ | 465 | 501 [19960] | 644 [15528] | 4432 |
| 7 | (10) | 3 | $7.8 \times 10^{-4}$ | 412 | 500 [20000] | 591 [16920] | 3080 |
| 8 | (13) | 4 | $5.4 \times 10^{-4}$ | 398 | 483 [20704] | 585 [17095] | 3609 |

Example 9

Preparation of a solution containing 4,7-bis(7,8-dicyclohexylmethylbenzo[1,2-b:4,3-b']dithiophene)benzo[c][1,2,5]thiadiazole having formula (3) for measuring the spectroscopic properties 1.9 mg ($2.1 \times 10^{-3}$ mmoles) of 4,7-bis(7,8-dicyclohexylmethylbenzo[1,2-b:4,3-b']dithiophene)benzo[c][1,2,5]thiadiazole having formula (3) obtained as described in Example 1, and 5 ml of anhydrous methylene chloride ($CH_2Cl_2$) were introduced, in an inert nitrogen ($N_2$) atmosphere, into a 10 ml tailed test-tube: the mixture obtained was left, under stirring, at room temperature (25° C.), for 16 hours, until a homogeneous solution was obtained. An aliquot of the solution obtained, containing $4.2 \times 10^{-4}$ moles/liter of the compound having formula (3), was subsequently transferred to a 1 cm quartz cell, and the absorption spectrum, the molar extinction coefficient (s), the emission spectrum and the Stokes shift were acquired, operating as described above: the values obtained are indicated in Table 3.

Examples 10-12

Preparation of Solutions Containing Compounds Having General Formula (I) for Measuring the Spectroscopic Properties According to the procedure described in Example 9, solutions were prepared in anhydrous methylene chloride ($CH_2Cl_2$) of the compounds having formula (5), formula (10) and formula (13), prepared according to what is described in Examples 2, 3 and 4, respectively.

The absorption spectrum, molar extinction coefficient ($\epsilon$), emission spectrum and Stokes shift, were acquired on each film thus obtained, operating as described above: the values obtained are indicated in Table 3.

Table 3 indicates, in order: the Example number (Example), the number referring to the formula of the compound used (Formula compound), the number of the example in which the compound was prepared (Example prep.), the concentration of compound in the film (C) expressed in moles/liter (moles/l), the value of the maximum of the lowest energy band in the absorption spectrum [$\lambda_{max}$ (ass.)] expressed in (nm) and in [$cm^{-1}$], the molar extinction coefficient ($\epsilon$) expressed in liters×moles$^{-1}$×cm$^{-1}$ (1×moles$^{-1}$×cm$^{-1}$), the value of the maximum of the highest energy band in the emission spectrum [$\lambda_{max}$ (emiss.)] expressed in (nm) and in [$cm^{-1}$], and finally the Stokes shift value expressed in ($cm^{-1}$).

TABLE 3

| Ex. | Formula compound | Example Prep. | C (moles/l) | $\lambda_{max}$ (ads) (nm) [cm$^{-1}$] | ($\epsilon$) (l × moli$^{-1}$ × cm$^{-1}$) | $\lambda_{max}$ (emiss.) (nm) [cm$^{-1}$] | Stokes shift (cm$^{-1}$) |
|---|---|---|---|---|---|---|---|
| 9 | (3) | 1 | 4.2 × 10$^{-4}$ | 498 [20080] | 22686 | 635 [15748] | 4332 |
| 10 | (5) | 2 | 7.5 × 10$^{-4}$ | 504 [19841] | 25613 | 795 [12579] | 7262 |
| 11 | (10) | 3 | 5.3 × 10$^{-4}$ | 498 [20080] | 24403 | 633 [15798] | 4282 |
| 12 | (13) | 4 | 3.8 × 10$^{-4}$ | 482 [20747] | 18248 | 611 [16367] | 4380 |

Examples 13-15

Determination of the Luminescence Quantum Efficiency ($\Phi$) in Solution of Compounds Having General Formula (I)

Using the solutions prepared according to what is described in Examples 9, 11 and 12 containing compounds having formula (3), formula (10) and formula (13), prepared according to what is described in Examples 1, 3 and 4, respectively, the luminescence quantum efficiency (0) was acquired, using Rhodamina 101 dissolved in ethyl alcohol, as external standard and operating as described above.

The values obtained are indicated in Table 4 which indicates, in order: the Example number (Example), the number referring to the formula of the compound used (Formula compound), the number of the example in which the compound was prepared (Example prep.), the concentration of compound in the film (C) expressed in moles/liter (moles/l), and finally the luminescence quantum efficiency ($\Phi$) expressed in percentage (%).

TABLE 4

| Examp. | Formula compound | Example prep. | C (moles/l) | $\Phi$ (%) |
|---|---|---|---|---|
| 9 | (3) | 1 | 4.2 × 10$^{-4}$ | 82 |
| 11 | (10) | 3 | 5.3 × 10$^{-4}$ | 79 |
| 12 | (13) | 4 | 3.8 × 10$^{-4}$ | 76 |

Example 16

6 g of polymethylmethacrylate (PMMA) Altuglas VSUVT 100 and 0.055 g (0.061 mmoles) of 4,7-bis(7,8-dicyclohexylmethylbenzo[1,2-b:4,3-b']dithiophene)benzo[c][1,2,5]thiadiazole having formula (3) obtained as described in Example 1, were dissolved in 30 ml of 1,2-diclorobenzene. The solution obtained was subsequently uniformly deposited on a sheet of polymethylmethacrylate Altuglas VSUVT 100 (PMMA) (dimensions 90×90×6 mm) with the use of, a Doctor Blade-type film applicator and the solvent was left to evaporate at room temperature (25° C.), under a light stream of air, for 24 hours. A transparent sheet was produced (sheet 1) having a red colour conferred by the film, whose thickness proved to range from 40 µm to 100 Ξm.

A photovoltaic cell IXYS-XOD17 having a surface of 1.2 cm$^2$ was then applied to one of the edges of the polymeric sheet.

The main side of the polymeric sheet [that coated with the thin film containing the compound having formula (3)] was then illuminated with a light source having a power equal to 1 sun (1000 W/m$^2$) and the electric power generated by the illumination, was measured.

The power measurements were carried out by covering, with an opaque coating (cover), surfaces having variable areas of the polymeric support, at an increasing distance from the edge on which the photovoltaic cells were fixed. These measurements under variable screening conditions allow the contribution of possible waveguide, edge or multiple diffusion effects due to the support, to be quantified and consequently subtracted.

FIG. 1 shows the curve relating to the value of the power (P) generated per unit of surface illuminated, expressed as mW/cm$^2$, in relation to the distance (d) of the cover from the edge of the support containing the solar cell, expressed in cm.

It can be seen that, in the absence of edge effects, the average power generated is equal to 0.11 mW/cm$^2$ (FIG. 1).

The invention claimed is:

1. A compound having general formula (I) or a mixture of compounds having general formula (I):

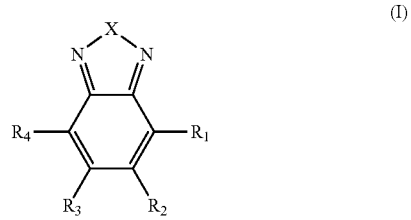

(I)

wherein:
X represents a heteroatom selected from the group consisting of oxygen (O), sulfur (S), selenium (Se), and tellurium (Te);
R1, R2, R3 and R4, the same or different from each other, represent a hydrogen atom; or they represent a halogen atom selected from the group consisting of fluorine, chlorine, and bromine; or they are selected from the group consisting of linear or branched C1-C20 alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, and cyano groups; or they are selected from the benzodithiophene groups consisting of general formula (II) and (III):

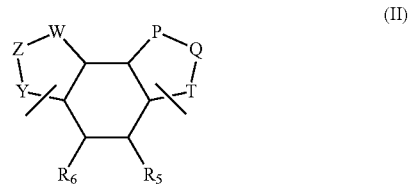

(II)

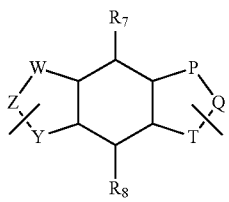

(III)

wherein:
- Y, Z, W, P, Q and T, each independently, represent a sulfur atom (S), with the proviso that:
  - at least one of P, Q and T and at least one of W, Z and Y, is a sulfur atom (S); and
  - in general formula (III), Q and Z do not contemporaneously represent a sulfur atom (S);
  - the remaining Y, Z, W, P, Q and T, represent a group —C—R9, —C—R10, —C—R11, —C—R12, so that the sum of the double carbon-carbon (C=C) bonds present in the two thiophene rings and in the benzene ring is equal to 5;
- R5, R6, R7, R8, R9, R10, R11 and R12, the same or different from each other, represent a hydrogen atom; or they represent a halogen atom selected from the group consisting of fluorine, chlorine and bromine; or they are selected from the group consisting of linear or branched C1-C20 alkyl groups, saturated or unsaturated, optionally containing heteroatoms, aryl groups optionally substituted, heteroaryl groups optionally substituted, cycloalkyl groups optionally substituted, heterocyclic groups, optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, and cyano groups;
  with the proviso that, in the case of R1 and R4, when the benzodithiophene group of general formula (II) or general formula (III) is present one of Q and Z represents the group —CH;
  or R5 and R6, can be optionally bound to each other so as to form, together with the other atoms to which they are bound, a cycle containing from 3 to 12 carbon atoms, saturated, unsaturated, or aromatic, optionally substituted with linear or branched C1-C20 alkyl groups, saturated or unsaturated, optionally containing heteroatoms, aryl groups optionally substituted, heteroaryl groups optionally substituted, cycloalkyl groups, optionally substituted, heterocyclic groups, optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, cyano groups, said cycle optionally containing heteroatoms selected from the group consisting of oxygen, sulfur, nitrogen, silicon, phosphorous, and selenium;
  or R1 and R2, R2 and R3, R3 and R4, can be optionally bound to each other so as to form, together with the other atoms to which they are bound, a cycle containing from 3 to 12 carbon atoms, saturated, unsaturated or aromatic, optionally substituted with linear or branched C1-C20 alkyl groups, optionally containing heteroatoms, aryl groups optionally substituted, heteroaryl groups optionally substituted, cycloalkyl groups optionally substituted, heterocyclic groups optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, cyano groups, said cycle optionally containing heteroatoms selected from the group consisting of oxygen, sulfur, nitrogen, silicon, phosphorous, and selenium;

with the proviso that at least two of R1, R2, R3 and R4 are selected from the benzodithiophene groups consisting of general formula (II) and (III).

2. The compound having general formula (I) or a mixture of compounds having general formula (I) according to claim 1, wherein R1 and R4 are selected from the benzodithiophene groups consisting of general formula (II) and (III).

3. A luminescent solar concentrator (LSC) including at least one compound having general formula (I) or at least a mixture of compounds having general formula (I), according to claim 1.

4. A solar device comprising a luminescent solar concentrator (LSC) according to claim 3.

5. The compound having general formula (I) or a mixture of compounds having general formula (I) according to claim 1 wherein both R1 and R4 are selected from the benzodithiophene group of general formula (II) in which one of Q and Z represents the group —CH.

6. The compound having general formula (I) or a mixture of compounds having general formula (I) according to claim 1 wherein both R1 and R4 are selected from the benzodithiophene group of general formula (III) in which one of Q and Z represents the group —CH.

7. A compound having general formula (I) or a mixture of compounds having general formula (I):

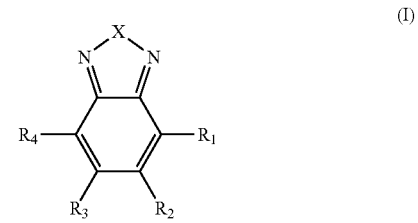

(I)

wherein:
- X represents a heteroatom selected from the group consisting of oxygen (O), sulfur (S), selenium (Se), and tellurium (Te);
- R1, R2, R3 and R4, the same or different from each other, represent a hydrogen atom; or they represent a halogen atom selected from the group consisting of fluorine, chlorine, and bromine; or they are selected from the group consisting of linear or branched C1-C20 alkyl groups, saturated or unsaturated, optionally containing heteroatoms, aryl groups optionally substituted, heteroaryl groups optionally substituted, cycloalkyl groups optionally substituted, heterocyclic groups optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, and cyano groups; or they are selected from the benzodithiophene groups consisting of general formula (II) and (III):

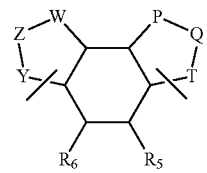

(II)

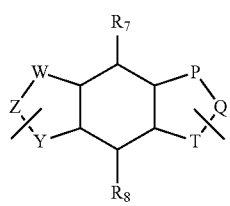

(III)

wherein:
Y, Z, W, P, Q and T, each independently, represent a sulfur atom (S), with the proviso that:
at least one of P, Q and T and at least one of W, Z and Y, is a sulfur atom (S); and
in general formula (III), Q and Z do not contemporaneously represent a sulfur atom (S);
the remaining Y, Z, W, P, Q and T, represent a group —C—R9, —C—R10, —C—R11, —C—R12, so that the sum of the double carbon-carbon (C=C) bonds present in the two thiophene rings and in the benzene ring is equal to 5;
R5, R6, R7, R8, R9, R10, R11 and R12, the same or different from each other, represent a hydrogen atom; or they represent a halogen atom selected from the group consisting of fluorine, chlorine and bromine; or they are selected from the group consisting of linear or branched C1-C20 alkyl groups, saturated or unsaturated, optionally containing heteroatoms, aryl groups optionally substituted, heteroaryl groups optionally substituted, cycloalkyl groups optionally substituted, heterocyclic groups, optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, and cyano groups;
with the proviso that in the case of R1 and R4, when the benzodithiophene group of general formula (II) or general formula (III) is present Q and Z are not substituted heteroaryl groups;
or R5 and R6, can be optionally bound to each other so as to form, together with the other atoms to which they are bound, a cycle containing from 3 to 12 carbon atoms, saturated, unsaturated, or aromatic, optionally substituted with linear or branched C1-C20 alkyl groups, saturated or unsaturated, optionally containing heteroatoms, aryl groups optionally substituted, heteroaryl groups optionally substituted, cycloalkyl groups, optionally substituted, heterocyclic groups, optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, cyano groups, said cycle optionally containing heteroatoms selected from the group consisting of oxygen, sulfur, nitrogen, silicon, phosphorous, and selenium;
or R1 and R2, R2 and R3, R3 and R4, can be optionally bound to each other so as to form, together with the other atoms to which they are bound, a cycle containing from 3 to 12 carbon atoms, saturated, unsaturated or aromatic, optionally substituted with linear or branched C1-C20 alkyl groups, optionally containing heteroatoms, aryl groups optionally substituted, heteroaryl groups optionally substituted, cycloalkyl groups optionally substituted, heterocyclic groups optionally substituted, trialkyl- or triaryl-silane groups, dialkyl- or diaryl-amine groups, dialkyl- or diaryl-phosphine groups, alkoxyl or aryloxyl groups, thioalkoxyl or thioaryloxyl groups, cyano groups, said cycle optionally containing heteroatoms selected from the group consisting of oxygen, sulfur, nitrogen, silicon, phosphorous, and selenium; with the proviso that at least one of R1, R2, R3 and R4 represent(s) a benzodithiophene group having general formula (II) or (III).

* * * * *